United States Patent [19]

Kikuchi et al.

[11] Patent Number: 5,118,508
[45] Date of Patent: Jun. 2, 1992

[54] PHARMACEUTICAL COMPOSITION

[75] Inventors: Yoshiaki Kikuchi; Takashi Osada, both of Tokyo, Japan

[73] Assignee: Showa Yakuhin Kako Co., Ltd., Tokyo, Japan

[21] Appl. No.: 651,931

[22] Filed: Feb. 7, 1991

[30] Foreign Application Priority Data

Feb. 7, 1990 [JP] Japan ................... 2-27861

[51] Int. Cl.$^5$ ............................. A61F 13/02
[52] U.S. Cl. .................... 424/448; 424/449; 424/447
[58] Field of Search ............. 424/448, 449, 447

[56] References Cited

U.S. PATENT DOCUMENTS

| 4,565,821 | 1/1986 | Chion | 514/323 |
| 4,593,048 | 6/1986 | Sato et al. | 514/778 |
| 4,710,497 | 12/1987 | Heller et al. | 514/221 |
| 4,752,612 | 6/1988 | Saito et al. | 514/420 |
| 4,863,952 | 9/1989 | Abe et al. | 514/423 |

FOREIGN PATENT DOCUMENTS

| 20063014 | 10/1982 | European Pat. Off. |
| 10156080 | 10/1985 | European Pat. Off. |
| 10253901 | 1/1988 | European Pat. Off. |
| 12598614 | 11/1987 | France |
| 2053681 | 2/1981 | United Kingdom |

OTHER PUBLICATIONS

Organic-Chemical Drugs and Their Synonyms, 6th edition, 1987, M. Negwer.

Primary Examiner—Thurman K. Page
Assistant Examiner—L. Horne
Attorney, Agent, or Firm—Oblon, Spivak, McClelland, Maier & Neustadt

[57] ABSTRACT

The present invention relates to a pharmaceutical composition in a form of a film. The composition comprises (a) a butyrophenone compound and (b) a vehicle comprising polyvinyl acetal diethylaminoacetate and polyvinyl pyrrolidone. The ratio of the compound to the vehicle is from 1% to 80% by weight based on the total weight of the vehicle and the ratio by weight of polyvinyl acetal diethylaminoacetate and polyvinyl pyrrolidone is from 1:9 to 9:1. The pharmaceutical composition can be applied to the skin of a patient for a long time and maintain a therapeutically effective blood level of the butyrophenone.

18 Claims, No Drawings

PHARMACEUTICAL COMPOSITION

BACKGROUND OF THE INVENTION

1. Field of the Invention

The present invention relates to a pharmaceutical composition comprising a butyrophenone compound which is useful as a cataplasm.

2. Description of the related Art

Butyrophenone compounds have antipsychotic effects by means of inhibiting dopamine action. The butyrophenones are mainly used for the treatment of schizophrenia. Further, the compounds have antiemetic effects by acting on chemoreceptor triger-zones.

Recently, adverse reactions to cancer chemotherapy such as, for example, nausea and emesis, have become clinical problems. For the treatment of such adverse reactions, amtiemetics have been frequently used. In general, since the antiemetics are administered orally, the administration of antiemetics has various disadvantages as follows:

(a) it is necessary for patients to take the drug at least three times a day, (b) it is difficult to control the blood level of the drug, which results in the possibility of causing extrapyramidal syndromes in the patient such as akathisia and psychotic disorders such as, for example, anxiety and nervousness when the blood level of the drug increases over a certain level, and (c) it is difficult to administer the drug orally to some patients who vomit frequently during intervals of continuous vomiting.

One attempt to solve the above-mentioned problems was to administer the drug percutaneously in a form of an external preparation. An example of such an external preparation is that using a gel-type vehicle comprising water and a water-soluble polymer such as, for example, hydroxypropylcellulose and polyvinyl alcohol. However, if the external preparation comprising the gel-type vehicle is prepared in a form of a pasty composition dispensed from a tube, it is difficult to determine a single dosage to be administered and the area of the skin of a patient to be applied with the preparation. On the other hand, if the external preparation using the gel-type vehicle is prepared in a form of a tape composition to be applied on the skin of a patient, the manufacturing cost becomes too high due to its complicated structure. Another example of the external preparation is a cataplasm comprising the drug dispersed or dissolved in a vehicle such as, for example, a rubber-based adhesive, an acrylic adhesive, a silicone adhesive, or a water-soluble polymer. However, these cataplasms are not able to attain high blood level of the drug due to a low percutaneous absorption of the drug. In addition, the use of the cataplasm comprising a water-soluble polymer is not convenient since the structure of drug-containing layer cannot be maintained because of sweating during the application of the cataplasm.

SUMMARY OF THE INVENTION

It is, therfore, an object of the present invention to provide a pharmaceutical composition comprising a butyrophenone compound together with a pharmaceutically acceptable carrier or coatings, which overcomes the above-described disadvantages.

It is another object of the present invention to provide a pharmaceutical composition comprising a butyrophenone compound together with a pharmaceutically acceptable carrier or coatings which is useful as a cataplasm.

The inventors have conducted various investigations and have found that a cataplasm in a form of a film comprising a butyrophenone compound and a filmy vehicle containing a film-forming polyvinyl acetal diethylaminoacetate and a water soluble polyvinyl pyrrolidone demonstrates excellent percutaneous absorption of the butyrophenone compound and accomplishes the goals of the present invention.

In accordance with the present invention, there is provided a pharmaceutical composition in a form of a film comprising (a) a butyrophenone compound and (b) a vehicle comprising polyvinyl acetal diethylaminoacetate and polyvinyl pyrrolidone, wherein the ratio of the compound to the vehicle is from 1% to 80% by weight based on the total weight of the vehicle and the ratio by weight of polyvinyl acetal diethylaminoacetate and polyvinyl pyrrolidone is from 1:9 to 9:1.

In accordance with the present invention, there is provided a cataplasm comprising (a) a butyrophenone compound, (b) a vehicle comprising polyvinyl acetal diethylaminoacetate and polyvinyl pyrrolidone, and (c) a backing sheet, wherein the ratio of the compound to the vehicle is from 1% to 80% by weight based on the total weight of the vehicle and the ratio by weight of polyvinyl acetal diethylaminoacetate and polyvinyl pyrrolidone is from 1:9 to 9:1.

In accordance with the present invention, there is provided a method for the treatment of schizophrenia comprising a step of administering to a mammal an effective amount of said pharmaceutical composition or said cataplasm.

In accordance with the present invention, there is also provided a method for the treatment of emesis comprising a step of administering to a mammal an effective amount of said pharmaceutical composition or said cataplasm.

DETAILED DESCRIPTION OF THE INVENTION

The butyrophenone compound used in preparing the pharmaceutical composition according to the present invention is represented by the following general formula (I):

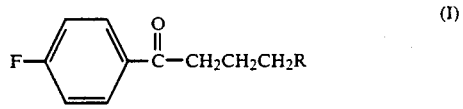

Examples of the butyrophenone compound used for the preparation of the pharmaceutical composition according to the present invention include those shown in the following table. The scope of the present invention is not limited to the use of these butyrophenones.

| R | generic name |
|---|---|
| 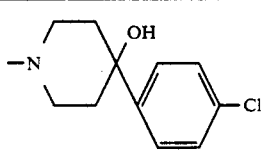 | haloperidol |

| R | generic name |
|---|---|
| 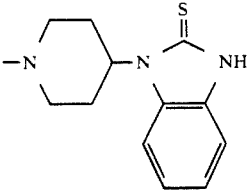 | timiperone |
| 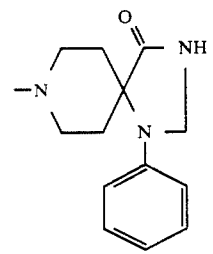 | spiroperidol |
| 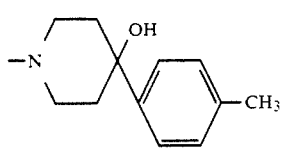 | methylperidol |
| 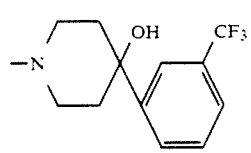 | trifluperidol |
| 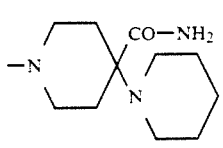 | floropipamide |
| 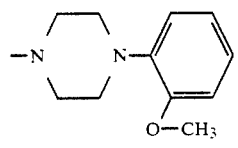 | fluanisone |
| 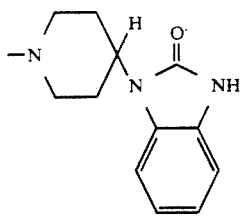 | benperidol |
| 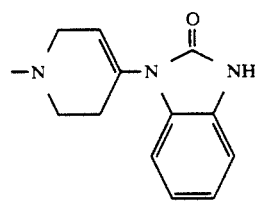 | droperidol |

The vehicle for carrying the pharmaceutical composition of the present invention comprises polyvinyl acetal diethylaminoacetate and polyvinyl pyrrolidone.

Polyvinyl acetal diethylaminoacetate used for the preparation of the pharmaceutical composition of the present invention is a slightly water-soluble polymer having film-forming properties. For example, polyvinyl acetal diethylaminoacetate having a molecular weight of from about 50,000 to about 70,000, preferably about 60,000, may be used. These compounds are available from Sankyo Co., Ltd. Japan.

Polyvinyl pyrrolidone used for the preparation of the pharmaceutical composition of the present invention is a water soluble polymer having film-formimg properties. For examples, polyvinyl pyrrolidone having an average molecular weight of from about 25,000 to about 1,200,000, may be used. Examples of the polymer include polyvinyl pyrrolidone K25, K30 and K90 (Japanese Pharmacopoeia XI).

The ratio of the polyvinyl acetal diethylaminoacetate to the Polyvinyl pyrrolidone in the vehicle is from 1:9 to 9:1 by weight, Preferably from 1:3 to 3:1 by weight. If a content of polyvinyl acetal diethylaminoacetate is less than the range defined above, the structure of the film formed may be altered by the patient's perspiration. On the other hand, if the content of polyvinyl pyrrolidone is less than the range defined above, the flexibility of the film may decrease. The rate of release of the butyrophenone compound can be controlled by changing the ratio of said polymers within the above range. For example, if haloperidol is used as a butyrophenone compound, a desirable result can be obtained if the ratio of polyvinyl acetal diethylaminoacetate to polyvinyl pyrrolidone is 1:1 by weight The butyrophenone compound may be contained in the pharmaceutical composition according to the present invention in an amount of from 1 to 80% by weight, preferably from 5 to 60% by weight, based on the total weight of the vehicle comprising polyvinyl acetal diethylaminoacetate and polyvinyl pyrrolidone. If the butyrophenone compound is contained in the pharmaceutical composition in an amount outside the above-defined range, the film-forming properties of the pharmaceutical composition may decrease.

The cataplasm of the present invention can be usually prepared by the following process which comprises the steps of dissolving polyvinyl acetal diethylaminoacetate and polyvinyl pyrrolidone a solvent to prepare a solution so that the solution contains the mixture of the polymers in the concentration of from 3% to 30% by weight, preferably from 8 % to 20% by weight; adding a butyrophenone compound to the solution obtained; applying the mixture to a suitable backing sheet; and subsequently removing the solvent. The pharmaceutical composition of the present invention may be prepared by the method described above which may further comprise the step of separating the pharmaceutical composition from the smooth plate such as, for example, a metal plate or a glass plate. Examples of the solvents to prepare a solution of the polymers include, for example, methanol or ethanol. According to the above-described method for preparing the cataplasm in a form of a film, the solvent can be removed at a relatively low temperature and there is needed only a short time for removing the solvent and drying the film formed. This leads to an advantage when preparing a pharmaceutical preparation containing an unstable butyrophenone under increased temperature.

Examples of the backing sheet include, for example, various types of non-woven fabric, woven fabric, spandex, flannel, a polyethylene film, a polyvinyl chloride film, an ethylene-vinyl acetate film, a polyurethane film, and a laminate film comprising the foregoing films.

The thickness of the pharmaceutical composition in a form of a film prepared by the above-described method may be from about 0.001 mm to about 4 mm, preferably from about 0.01 mm to 1 mm. For example, where 1 g of haloperidol, 10 g of polyvinyl acetal diethylaminoacetate, and 10 g of polyvinyl pyrrolidone are used for the preparation of the Pharmaceutical composition of the present invention, a cataplasm having the thickness of 0.01 mm and the area of 200 $cm^2$ can be obtained. The thickness of the pharmaceutical composition according to the present may have constant thickness all over the composition or the thickness of the composition may be varied from portion to portion.

The pharmaceutical composition of the present invention may be optionally applied on an adhesive sheet. Examples of the adhesive sheet include a plastic film such as, for example, a plastic film coated with an adhesive such as, for example, a rubber adhesive, an acrylic adhesive, and a silicone adhesive, and examples of the plastic film include, for example, a polyethylene film, a polypropylene film, and a Polyester film.

If desired, various kinds of additives may be added for the preparation of the pharmaceutical composition of the present invention. Examples of the additives include preservatives such as, for example, parahydroxybenzoic acid derivatives, benzyl alcohol, phenol and cresol; stabilizers such as, for example, sodium pyrosulfite, sodium sulfite, rongalite, and ascorbic acid; alcohols and derivatives thereof; organic acids and salts thereof; nitrogen-containing organic compounds; solubilizers such as, for example, nonionic surfactants; polyhydric alcohols such as, for example, glycols and triols; aliphatic carboxylic acids and salts thereof; and plasticizers such as, for example, sacchrides. The amount of the additive may generally be from 0.1 to 80% by weight based on total weight of the vehicle.

The pharmaceutical composition or the cataplasm according to the present invention can be applied to the chest, the back, the neck and the other part of a body of a patient for the treatment of vomiting, schizophrenia, mania and the like. The butyrophenone compound contained in the applied cataplasm can be absorbed percutaneously so that a constant blood concentration of the drug can be maintained for a long time. In general, the pharmaceutical composition may be administered to a patient an effective amount for the treatment of said diseases. For example, the effective amount may correspond to the usual oral dosage of a butyrophenone which may be between 3 to 400 mg to an adult patient per day. The dosage can be varied according to the age or condition of the patient. For example, the pharmaceutical composition or the cataplasm of the present invention can be cut in a size so that a therapeutically effective amount of the butyrophenone is contained in the piece of the cataplasm before applying to the skin of a patient.

The pharmaceutical composition or the cataplasm according to the present invention can maintain a therapeutically effective blood level of the butyrophenone by being applied to the skin of a patient only once a day, which makes it easy for a vomiting patient to be frequently treated by the pharmaceutical composition of the present invention. Further, the pharmaceutical composition or the cataplasm according to the present invention can be conveniently applied for a Prolonged time without any irritation, and the dosage of the composition to be administered can be determined more precisely than external preparations disclosed in the prior art which comprise butyrophenones together with an ointment or a gel-type vehicle. Furthermore, the pharmaceutical composition or the cataplasm according to the present invention is clinically convenient since the structure of the film is not altered during its application.

EXAMPLE

The present invention will be further explained by way of examples. These examples are intended to be illustrative only and are not intended to limit the scope of the present invention. Also, parts and percentages are by weight unless otherwise indicated.

Example 1

A cataplasm was prepared by dissolving 2 g of polyvinyl acetal diethylaminoacetate AEA (available from Sankyo Co., Ltd., Japan) and 2g of polyvinyl pyrrolidone K90 (Japanese Pharmacopoeia XI) in the ratio of 1:1 by weight in 16g of ethanol, adding 1 g of haloperidol (butyrophenone antipsychotic) to the solution, applying the resulting mixture on the smooth glass plate, evaporating the solvent to form a film composition in a size of about 10 cm $\times$ 20 cm $\times$ 0.01 cm, and then applying the film to an adhesive sheet (a laminated polyethylene film with an acrylic adhesive coating).

Comparative Example 1

A cataplasm was prepared in accordance with the procedure described in Example 1 except that 1 g of haloperidol was added to 20g of 10% by weight aquarous polyvinyl alcohol solution.

Comparative Example 2

The same size cataplasm as that of Example 1 was prepared by adding 1 g of haloperidol to 2 g of a rubber adhesive comprising 10 parts of natural gum, 5 parts of ester gum AAG (available from Arakawa kako Co.) and 7.5 parts of Alukon P-100 (available from Arakawa kako Co. ), and applying the mixture obtained on a backing sheet (a laminated polyethylene film).

Comparative Example 3

The same size cataplasm as that of Example 1 was prepared by adding 1 g of haloperidol to 2 g of an acrylic adhesive comprising a copolymer of 95% of isoamyl acrylate and 5% of methacrylic acid (average degree of polymerization of about 1000), and applying the mixture obtained on a backing sheet (a laminated polyethylene film).

Comparative Example 4

The same size cataplasm as that of Example 1 was prepared by adding 1 g of haloperidol to 2g of a silicone adhesive DOW CORNING 355 (available from Dow Corning Co. Ltd.) and applying the resulting mixture on a backing sheet (a laminated polyethylene film).

Example 2

The cataplasms of the present invention were prepared in accordance with the procedure of Example 1 except that polyvinyl acetal diethylaminoacetate and polyvinyl pyrrolidone were dissolved in ethanol in a different ratio and haloperidol, timiperone, and spiroperidol were used as butyrophenones.

Further, a cataplasm free from polyvinyl pyrrolidone (Comparative Example 5) and a cataplasm free from polyvinyl acetal diethylaminoacetate (Comparative Example 6) were prepared in accordance with the procedure of Example 1.

Comparative Example 7

Cataplasms were prepared in accordance with the same procedure of Example 1 except that 1 g of haloperidol, timiperone, or spiroperidol was added to 20 g of a 10% aquarous solution of polyvinyl alcohol.

Experiment 1

The cataplasms prepared in Examples 1 and 2, Comparative Examples 1, 2, 3, 4, 5, 6, and 7 were cut in a piece having the size of 1 cm × 1 cm (containing 0.6 mg of a butyrophenone compound) and then applied to the forearms of adult male volunteers. After 8 hours, the amount of the butyrophenone compound retaining in the cataplasm was determined to calculate a percutaneous absorption of the butyrophenone compound (%). Degree of skin-irritation was estimated by observing the region applied by the cataplasm after 8 hours from the application. The results obtained are showed in Tables 1 and 2.

TABLE 1

|  | Vehicle | Percutaneous absorption of haloperidol(%) | Skin-irritation |
|---|---|---|---|
| Example 1 | Mixed vehicle of the present invention | 39.2 | (−) |
| Comparative Example 1 | PVA vehicle | 11.7 | (−) |
| Comparative Example 2 | Rubber vehicle | 18.0 | (+) |
| Comparative Example 3 | Acrylic vehicle | 6.5 | (−) |
| Comparative Example 4 | Silicone vehicle | 0.0 | (−) |

(+) irritation was observed; (−) irritation was not observed

The cataplasm of Example 1 showed a higher percutaneous absorption of haloperidol than those of Comparative Examples 1, 2, 3, and 4. Furthermore, the cataplasm of Example 1 showed no skin-irritation, which revealed that the vehicle comprised in the irritation to human skin.

TABLE 2

|  | PD: PVP | Percutaneous absorption of HAL (%) | Percutaneous absorption of TIM (%) | Percutaneous absorption of SPI (%) |
|---|---|---|---|---|
| Comparative Example 1 | 4:0 | 6.1 | 7.4 | 1.3 |
| Example 2 | 9:1 | 16.4 | 10.5 | 10.8 |
|  | 3:1 | 22.1 | 12.5 | 13.5 |
|  | 1:1 | 39.2 | 28.5 | 21.5 |
|  | 1:3 | 33.5 | 30.7 | 13.6 |
|  | 1:9 | 17.1 | 16.2 | 13.6 |
| Comparative Example 6 | 0:4 | 4.4 | 12.0 | 8.3 |
| Comparative Example 7 | PVA | 11.7 | 7.0 | 4.8 |

PD: Polyvinyl acetal diethylaminoacetate
PVP: Polyvinyl pyrrolidone
PVA: Polyvinyl alcohol
HAL: Haloperidol
TIM: Timiperone
SPI: Spiroperidol As shown in Table 2, the cataplasms of Examples 2, comprising polyvinyl acetal diethylaminoacetate and polyvinyl pyrrolidone in a ration of from 1:9 to 9:1, showed a higher percutaneous absorption of each butyrophenone compound than those of Comparative Examples 5, 6, and 7. Thus, it can be concluded that the appropriate ratio by weight of polyvinyl acetal diethylaminoacetate to polyvinyl pyrrolidone may range from 1:9 to 9:1, more preferably from 1:3 to 3:1. Furthermore, the vehicle comprised in the cataplasm of Example 2 had a synergistic increase of the percutaneous absorption of the butyrophenone compound compared with those of Comparative Examples 5 and 6 comprising polyvinyl acetal diethylaminoacetate Or polyvinyl pyrrolidone alone as a vehicle.

Example 3

A cataplasm was prepared in accordance with the procedure of Example 1 except that 2 g of polyvinyl acetal diethylaminoacetate and 2 g of polyvinyl pyrrolidone in the ratio of 1:1 by weight were dissolved in 16 g of ethanol, and 1 g of timiperone was added to the solution.

Comparative example 8

The same size cataplasm as that of Example 1 was prepared in accordance with the procedure of Example 1 except that 1 g of timiperone was added to 20 g of 10% aqueous solution of polyvinyl alcohol.

Experiment 2

Each of the cataplasms prepared in Example 3 and Comparative Example 8 was cut in a piece having the size of 4cm × 5cm (containing 12mg of timiperone) and the piece was applied to the pectoral region of adult volunteers. After 8 hours and 24 hours, the blood of each subject was collected and the plasma levels of timiperone were measured by HPLC method to obtain the percutaneous absorption of timiperone. The results are shown in Table 3.

In addition, each of the cataplasms prepared in Example 3 and Comparative Example 8 was cut in a piece having the size of 2 cm × 2 cm (containing 2.4 mg of timiperone) and the pieces were applied to the depilated abdominal skin of a 8-week old male Wister rat. After 4, 6, 8 and 24 hours, the blood of the rats were collected and the plasma levels of timiperone were measured by the same manner as the above to obtain a percutaneous absorption of timiperone. The results are shown in Table 4.

TABLE 3

| Applying time (hour) | TIM Concentration in plasma (ng/ml) | | Percutaneous absorption of TIM (%) | |
|---|---|---|---|---|
|  | Example 3 | Comparative Example 8 | Example 3 | Comparative Example 8 |
| 8 | 0.6 | 0.3 | 11.2 | 2.4 |
| 24 | 1.8 | 1.1 | 30.0 | 23.2 |

TABLE 4

| Applying time (hour) | TIM Concentration in plasma (ng/ml) | | Percutaneous absorption of TIM (%) | |
|---|---|---|---|---|
|  | Example 3 | Comparative Example 8 | Example 3 | Comparative Example 8 |
| 4 | 2.5 | 1.2 | 20.3 | 14.2 |
| 6 | 4.1 | 2.8 | 24.5 | 18.1 |
| 8 | 3.0 | 2.3 | 24.8 | 19.4 |
| 24 | 0.9 | 0.3 | 24.9 | 18.7 |

As shown in Table 3 and 4, higher plasma level of timiperone and higher percutaneous absorption of timiperone was observed with respect to the cataplasm prepared in Example 3 compared with those prepared in Comparative Example 8 in the adult male volunteers as well as in rats.

Experiment 3

A release test was performed in a horizontal membrane type cell by placing each 1 cm × 1 cm piece of the cataplasms prepared in example 2, Comparative Examples 5 and 6 (containing 0.6 mg of timiperone) above a membrane filter, using 40ml of a pH 6 phosphate buffer as a receptor phase. Table 5 shows a rate of release of timiperone (%) at 1.5, 2.0, 4.0, 8.0 and 24 hours. The rate of release was increased in the case where the ratio by weight of polyvinyl acetal diethylaminoacetate to polyvinyl pyrrolidone was from 3:1 to 1:3.

TABLE 5

| PD:PVP | Rate of release of TIM (%) hour | | | | |
|---|---|---|---|---|---|
| | 1.5 | 2.0 | 4.0 | 8.0 | 24.0 |
| 4:0 | 7.2 | 7.8 | 10.1 | 11.1 | 20.3 |
| 3:1 | 16.8 | 19.5 | 27.5 | 32.3 | 36.1 |
| 1:1 | 26.5 | 30.0 | 37.3 | 39.1 | 40.9 |
| 1:3 | 28.1 | 32.8 | 37.7 | 39.9 | 41.5 |
| 0:4 | 7.6 | 8.2 | 11.0 | 12.3 | 24.9 |

In various ratios of the polyvinyl acetal diethylaminoacetate to polyvinyl pyrrolidone, the same tendency is observed both in the rates Of release of TIM shown in Table 5 and the percutaneous absorption of TIM shown in Table 2. This suggests that percutaneous absorption of the butyrophenone compound depends on the release of the butyrophenone compound from the vehicle. Thus, release of the butyrophenone compound can be controlled by varying the ratio of polyvinyl acetal diethylaminoacetate to polyvinyl pyrrolidone.

Vertical sliced sections of the vehicle film of the cataplasm at the start and the end of the release test were microscopically examined with magnifying power of 100. The film was swelled by water at the end of the release test and a number of micro-holes formed by the release of the water-soluble polyvinyl pyrrolidone polymer and the butyrophenone compound were observed. This shows that the slightly water-soluble matrix comprising polyvinyl acetal diethylaminoacetate in the vehicle still retained in the film and prevented the film from being destroyed by water at the end of the release test.

The cataplasm according to the present invention is the preparation useful for the percutaneous absorption of the butyrophenone compound. By using the cataplasm according to the present invention, the release of the butyrophenone compound can be controlled. Further the use of the slightly water-soluble polymer as a vehicle in the cataplasm of the present invention avoids the destruction of the base film. The present invention still provides a quick method of administering the butyrophenone compound. Furthermore the cataplasm according to the present invention can be applied to the skin of a patient for a long time because it dose not irritate the skin. A therapeutically effective blood level of the butyrophenone compound can be maintained for a long time because of its high rate of release of the butyrophenone compound.

While the present invention has been illustrated by means of several preferred embodiments, one of ordinary skill in the art will recognize that improvements and modifications may be made within the scope of the present invention which is determined solely by the appended claims.

We claim:

1. A pharmaceutical composition in a form of a film comprising (a) a butyrophenone compound selected from the group consisting of ahloperidol, timiperone, spiroperidol, methylperido, trifluorperidol, b enperidol and dropericol and (b) a vehicle comprising polyvinyl acetal diethylaminoacetate and polyvinyl pyrrolidone, wherein the ratio of the compound to the vehicle is from 1% to 80% by weight based on the total weight of the vehicle and the ratio by weight of polyvinyl acetal diethylaminoacetate and polyvinyl pyrrolidone is from 1:9 to 9:1.

2. The pharmaceutical composition according to claim 1 wherein the film has a thickness of from about 0.01 mm to 4 mm.

3. A method for the treatment of emesis comprising the step of administering to a mammal an effective amount of a cataplasm comprising (a) a butyrophenone compound, (b) a vehicle comprising polyvinyl acetal diethylaminoacetate and polyvinyl pyrrolidone, and (c) a backing sheet, wherein the ratio of the compound to the vehicle is from 1% to 80% by weight based on the total weight of the vehicle and the ratio by weight of polyvinyl acetal diethylaminoacetate and polyvinyl pyrrolidone is from 1:9 to 9:1.

4. The pharmaceutical composition according to claim 1 wherein the polyvinyl acetal diethylaminoacetate has a molecular weight of from 50,000 to 70,000.

5. The pharmaceutical composition according to claim 1 wherein the polyvinyl pyrrolidone has an average molecular weight of from 25,000 to 1,200,000.

6. The pharmaceutical composition according to claim 1 wherein the butyrophenone compound is dispersed in the vehicle to form the film.

7. A cataplasm comprising (a) a butyrophenone compound, (b) a vehicle comprising polyvinyl acetal diethylaminoacetate and polyvinyl pyrrolidone, and (c) a backing sheet, wherein the ratio of the compound to the vehicle is from 1% to 80% by weight based on the total weight of the vehicle and the ratio by weight of polyvinyl acetal diethylaminoacetate and polyvinyl pyrrolidone is from 1:9 to 9:1.

8. The cataplasm according to claim 7 wherein the film has a thickness of from about 0.01 mm to 4 mm.

9. The cataplasm according to claim 7 wherein the film is applied to the backing sheet.

10. The cataplasm according to claim 7 wherein the film is applied to an adhesive sheet.

11. The cataplasm according to claim 7 wherein the backing sheet is selected from the group consisting of a unwoven fabric, woven fabric, spandex, flannel, a polyethylene film, a polyvinyl chloride film, a ethylene-vinyl acetate film, a polyurethane film and a laminate thereof.

12. The cataplasm according to claim 7 where the butyrophenone compound is selected from the group consisting of haloperidol, timiperone, spiroperidol, methylperidol, trifluperidol, floropipamide, fluanisone, benperidol and droperidol.

13. The cataplasm according to claim 7 wherein the polyvinyl acetal diethylaminoacetate has a molecular weight of from 50,000 to 70,000.

14. The cataplasm according to claim 7 wherein the polyvinyl pyrrolidone has an average molecular weight of from 25,000 to 1,200,000.

15. The cataplasm according to claim 7 wherein the butyrophenone compound is dispersed in the vehicle to form the film.

16. A method for the treatment of schizophrenia comprising the step of administering to a mammal an effective amount of a pharmaceutical composition in a form of a film comprising (a) a butyrophenone compound and (b) a vehicle comprising polyvinyl acetal diethylaminoacetate and polyvinyl pyrrolidone, wherein the ratio of the compound to the vehicle is from 1% from 80% by weight based on the total weight of the vehicle and the ratio by weight of polyvinyl acetal diethylaminoacetate and polyvinyl pyrrolidone is from 1:9 to 9:1.

17. A method for the treatment of schizophrenia comprising the step of administering to a mammal an effective amount of a cataplasm comprising (a) a butyrophenone compound, (b) a vehicle comprising polyvinyl acetal diethylaminoacetate and polyvinyl pyrrolidone, and (c) a backing sheet, wherein the ratio of the compound to the vehicle is from 1% to 80% by weight based on the total weight of the vehicle and the ratio by weight of polyvinyl acetal diethylaminoacetate and polyvinyl pyrrolidone is from 1:9 to 9:1.

18. A method for the treatment of emesis comprising the step of administering to a mammal an effective amount of a pharmaceutical composition in a form of a film comprising (a) a butyrophenone compound and (b) a vehicle comprising polyvinyl acetal diethylaminoacetate and polyvinyl pyrrolidone, wherein the ratio of the compound to the vehicle is from 1% to 80% by weight based on the total weight of the vehicle and the ratio by weight of polyvinyl acetal diethylaminoacetate and polyvinyl pyrrolidone is from 1:9 to 9:1.

* * * * *